(12) United States Patent
Lee et al.

(10) Patent No.: US 11,298,039 B2
(45) Date of Patent: Apr. 12, 2022

(54) BIOMETRIC INFORMATION MEASURING SENSOR, BIOMETRIC INFORMATION MEASURING SYSTEM, AND METHOD OF MEASURING BIOMETRIC INFORMATION USING THE SENSOR

(71) Applicant: Samsung Electronics Co., Ltd., Gyeonggi-do (KR)

(72) Inventors: Seung-min Lee, Seoul (KR); Seong-je Cho, Gyeonggi-do (KR); Hyoung-seon Choi, Seoul (KR); Young-jae Oh, Gyeonggi-do (KR); Chul-ho Cho, Gyeonggi-do (KR); Sun-tae Jung, Gyeonggi-do (KR); Jae-geol Cho, Gyeonggi-do (KR)

(73) Assignee: Samsung Electronics Co., Ltd

( * ) Notice: Subject to any disclaimer, the term of this patent is extended or adjusted under 35 U.S.C. 154(b) by 1502 days.

(21) Appl. No.: 15/091,909

(22) Filed: Apr. 6, 2016

(65) Prior Publication Data

US 2016/0302687 A1    Oct. 20, 2016

Related U.S. Application Data

(60) Provisional application No. 62/149,175, filed on Apr. 17, 2015.

(30) Foreign Application Priority Data

Oct. 21, 2015    (KR) .......................... 10-2015-0146659

(51) Int. Cl.
*A61B 5/05* (2021.01)
*A61B 5/00* (2006.01)
(Continued)

(52) U.S. Cl.
CPC ............. *A61B 5/05* (2013.01); *A61B 5/14865* (2013.01); *A61B 5/24* (2021.01); *A61B 5/6848* (2013.01)

(58) Field of Classification Search
CPC ......... A61B 5/05; A61B 5/04; A61B 5/14865; A61B 5/6848
See application file for complete search history.

(56) References Cited

U.S. PATENT DOCUMENTS 4,969,468 A  *  11/1990  Byers ................... A61B 5/0422
                                                       29/829
7,344,499 B1    3/2008  Prausnitz et al.
(Continued)

FOREIGN PATENT DOCUMENTS

KR    1020120006293    1/2012
WO    WO 2008/100118    8/2008

OTHER PUBLICATIONS

International Search Report dated Jul. 6, 2016 issued in counterpart application No. PCT/KR2016/004005, 14 pages.
(Continued)

*Primary Examiner* — Linda C Dvorak
*Assistant Examiner* — Annabeth E Rodriguez
(74) *Attorney, Agent, or Firm* — The Farrell Law Firm, P.C.

(57) ABSTRACT

A biometric information measuring sensor is provided that includes a base comprising a plurality of bio-marker measuring areas and a plurality of electrodes. Each of the plurality of electrodes is disposed on a respective one of the plurality of bio-marker measuring areas, and each of the plurality of electrodes includes a working electrode and a counter electrode spaced apart from the working electrode. The biometric information measuring sensor also includes a plurality of needles. Each of the needles is disposed on a
(Continued)

respective one of the plurality of electrodes. Two or more of the plurality of needles have different lengths.

14 Claims, 10 Drawing Sheets

(51) Int. Cl.
*A61B 5/1486* (2006.01)
*A61B 5/24* (2021.01)

(56) References Cited

U.S. PATENT DOCUMENTS

| | | | |
|---|---|---|---|
| 8,359,083 B2 * | 1/2013 | Clark | A61B 5/685 |
| | | | 600/378 |
| 8,956,545 B2 | 2/2015 | Jung et al. | |
| 2002/0091312 A1 | 7/2002 | Berner et al. | |
| 2008/0138583 A1 * | 6/2008 | Bhandari | A61M 37/0015 |
| | | | 428/156 |
| 2009/0099427 A1 * | 4/2009 | Jina | A61B 17/205 |
| | | | 600/309 |
| 2011/0144466 A1 * | 6/2011 | Zhang | A61B 5/6849 |
| | | | 600/347 |
| 2014/0336487 A1 * | 11/2014 | Wang | A61B 5/150984 |
| | | | 600/352 |

OTHER PUBLICATIONS

Korean Office Action dated Nov. 23, 2021 issued in counterpart application No. 10-2015-0146659, 13 pages.

\* cited by examiner

BIOMETRIC INFORMATION MEASURING SENSOR, BIOMETRIC INFORMATION MEASURING SYSTEM, AND METHOD OF MEASURING BIOMETRIC INFORMATION USING THE SENSOR

PRIORITY

This application claims priority under 35 U.S.C. § 119(e) to U.S. Provisional Application No. 62/149,175, filed in the U.S. Patent and Trademark Office on Apr. 17, 2015, and under 35 U.S.C. § 119(a) to Korean Patent Application No. 10-2015-0146659, filed in the Korean Intellectual Property Office on Oct. 21, 2015, the contents of which are incorporated herein by reference.

BACKGROUND

1. Field of the Disclosure

The present disclosure relates generally to a biometric information measuring sensor, and more particularly, to a biometric information measuring sensor having micro-needles for insertion into a body and a method of measuring biometric information using the biometric information measuring sensor.

2. Description of the Related Art

Methods of detecting biometric information may be divided into invasive methods and noninvasive methods. Various types of apparatuses for measuring biometric information have been developed and may be used depending on the type of biometric information to be measured.

In order to detect a status change in a specimen, an accurate detection of bio-markers is required. Bio-markers are biological indices inside the specimen. Specifically, the presence of and concentration changes in biological analytes, or bio-markers, are measured to objectively determine a status change of the specimen.

To measure the presence of and concentration changes in bio-markers existing inside a body of the specimen, blood may be collected from the specimen. However, repeated collection of blood from the specimen may be painful and an accurate analysis on changes of biological analytes may be difficult.

SUMMARY

The present disclosure has been made to address at least the above problems and/or disadvantages and to provide at least the advantages described below. Accordingly, an aspect of the present disclosure provides a biometric information measuring sensor, having a structure capable of measuring a presence of and concentration changes in bio-markers that exist inside the specimen.

According to an embodiment of the present disclosure, a biometric information measuring sensor is provided that includes a base having a plurality of bio-marker measuring areas and a plurality of electrodes. Each of the plurality of electrodes is disposed on a respective one of the plurality of bio-marker measuring areas, and each of the plurality of electrodes includes a working electrode and a counter electrode spaced apart from the working electrode. The biometric information measuring sensor also includes a plurality of needles. Each of the needles is disposed on a respective one of the plurality of electrodes. Two or more of the plurality of needles have different lengths.

According to another embodiment of the present disclosure, a biometric information measuring system is provided that includes a biometric information measuring sensor that includes a base with a plurality of bio-marker measuring areas, a plurality of electrodes, and a plurality of needles. Each of the plurality of electrodes is disposed on a respective one of the plurality of bio-marker measuring areas. Each of the plurality of electrodes includes a working electrode and a counter electrode spaced apart from the working electrode. Each of the plurality of needles is disposed on a respective one of the plurality of electrodes. Two or more of the plurality of needles have different lengths. The system also includes a terminal unit configured to calculate biometric information of a specimen from an electric signal transmitted from the biometric information measuring sensor.

According to another embodiment of the present disclosure, a method of measuring biometric information using a biometric information measuring sensor is provided. The biometric information measuring sensor is attached to a specimen. Electric signals are received that are detected by each of a plurality of needles of the biometric information measuring sensor that are inserted into the specimen, Two or more of the plurality of needles have different lengths. Bio-marker concentrations corresponding to the electric signals are measured.

BRIEF DESCRIPTION OF THE DRAWINGS

The above and other aspects, features, and advantages of the present disclosure will be more apparent from the following description when taken in conjunction with the accompanying drawings in which.

DETAILED DESCRIPTION

Figure 1A:
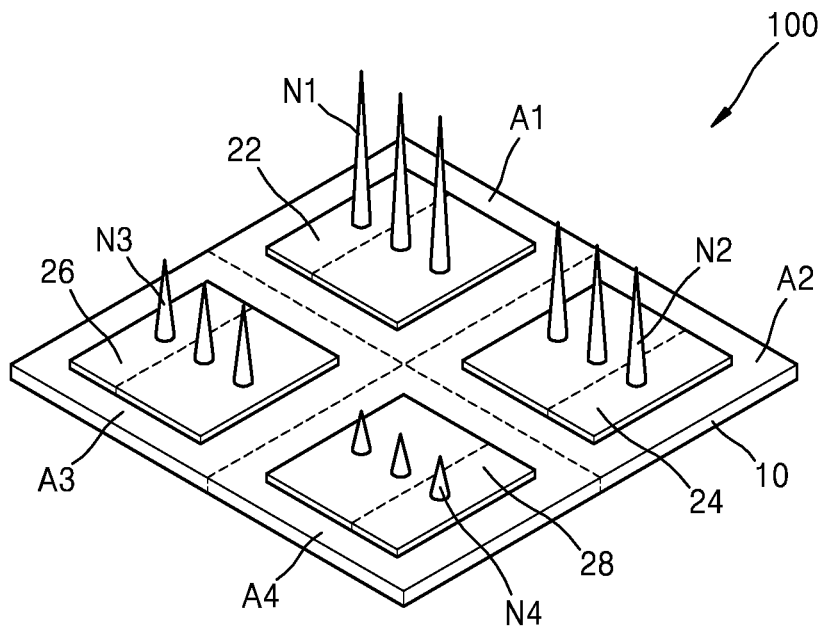
FIG. 1A is a diagram illustrating a biometric information measuring sensor, according to an embodiment of the present disclosure.

Embodiments of the present disclosure are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present disclosure.

Expressions such as "at least one of", when preceding a list of elements, modify the entire list of elements and do not modify the individual elements of the list.

Sizes or thicknesses of components in the drawings may be exaggerated for convenience of explanation. Specifically, since sizes and thicknesses of components in the drawings are arbitrarily illustrated for convenience of explanation, the following embodiments are not limited thereto. Terms used herein are merely used to describe embodiments, and are not intended to limit the inventive concept. As used herein, singular forms "a," "an", and "the" are intended to include the plural forms as well, unless the context clearly indicates otherwise.

FIG. 1A is a diagram illustrating a biometric information measuring sensor, according to an embodiment of the present disclosure.

Referring to FIG. 1A, a biometric information measuring sensor 100 includes a base 10 formed of an insulation material, and including at least one bio-marker measuring area. For example, in FIG. 1A, the base 10 has four bio-marker areas: a first area A1; a second area A2; a third area A3; and a fourth area A4. However, the number of bio-marker measuring areas is not limited thereto. A first electrode 22 is arranged on the first area A1. A first needle N1, which includes at least one needle with a probe shape to be inserted into a specimen, is arranged on the first electrode 22. A second electrode 24 is arranged on a second area A2. The second electrode 24 includes a second needle N2. A third electrode 26 is arranged on a third area A3. The third electrode 26 includes a third needle N3. A fourth electrode 28 is arranged on a fourth area A4. The fourth electrode 28 includes a fourth needle N4.

The first electrode 22 includes a working electrode that includes an enzyme capable of detecting a bio-marker, and a counter electrode spaced apart from the working electrode. The first electrode 22 may selectively include a reference electrode. The first needle N1 is arranged on the working electrode and the counter electrode, or the reference electrode, and the enzyme capable of detecting the bio-marker is coated only on the first needle N1 when arranged on the working electrode, which is described in greater detail below.

The above description of the first electrode 22 may also be applied to the second electrode 24, the third electrode 26 and the fourth electrode 28. Specifically, the second electrode 24, the third electrode 26, and the fourth electrode 28 may include the working electrode and the counter electrode spaced apart from the working electrode, and may selectively further include the reference electrode. Additionally, the second needle N2, the third needle N3, and the fourth needle N4 may be arranged on the working electrode and the counter electrode. The second needle N2, the third needle N3 and the fourth needle N4 may be coated with an enzyme capable of detecting the bio-marker.

The first needle N1, the second needle N2, the third needle N3, and the fourth needle N4 are arranged to have different heights, as shown in FIG. 1A. Specifically, needles N1, N2, N3, and N4 have different respective lengths. A length of the first needle N1 is longest, and lengths decrease in an order of the second needle N2, the third needle N3, and the fourth needle N4. Needles N1, N2, N3, and N4 may penetrate or may be inserted into a surface of the specimen at the time of biometric information measurement, and may measure a presence of the bio-marker and bio-marker concentration after having penetrated or been inserted into the surface of the specimen.

In FIG. 1A, lengths of respective needles N1, N2, N3, and N4 are each shown to be different, however, they are not limited thereto. At least some of the needles N1, N2, N3, and N4 may have different lengths, and the remaining needles may have same lengths. For example, the length of the first needle N1 is longer than the remaining needles N2, N3, and N4, and lengths of the second needle N2, the third needle N3, and the fourth needle N4 may be substantially the same.

In FIG. 1A, the first area A1 through the fourth area A4, which are bio-marker measuring areas on the base 10 of the biometric information measuring sensor 100, have a 2×2 array structure, however, it is not limited thereto. The structure may be in a form of a 2×3 array, a 3×3 array, a 4×2 array, a 4×3 array, a 4×4 array, etc., and the first area A1 through the fourth area A4 may also have a linear type array structure.

Figure 1B:
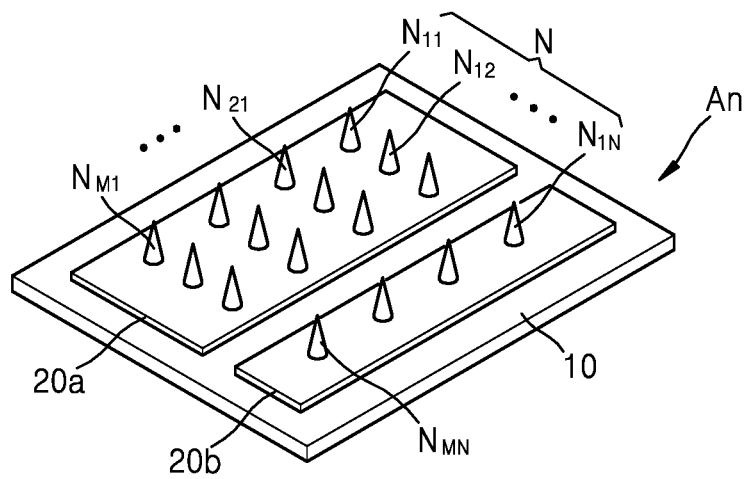
FIG. 1B is a diagram illustrating a bio-marker measuring area of the biometric information measuring sensor, according to an embodiment of the present disclosure.

FIG. 1B is a diagram illustrating a bio-marker measuring area of the biometric information measuring sensor, according to an embodiment of the present disclosure.

Referring to FIG. 1B, an $n^{th}$ area An, which is the bio-marker measuring area, includes a counter electrode 20a and a working electrode 20b. A needle N, which includes a plurality of needles, is arranged on the counter electrode 20a and the working electrode 20b. The number of needles arranged on the needle N is not limited, and needles may be arranged in various arrays on the counter electrode 20a and the working electrode 20b. For example, the needle N may include N (where N is an integer) needles $N_{11}, N_{12} \ldots, N_{1N}$ in one direction, and may include M (where M is an integer) needles $N_{11}, N_{21} \ldots, N_{M1}$ in another direction, and thus, may have an N*M array of needles. However, an array shape of needles of the needle N is not limited thereto.

Figure 2A:
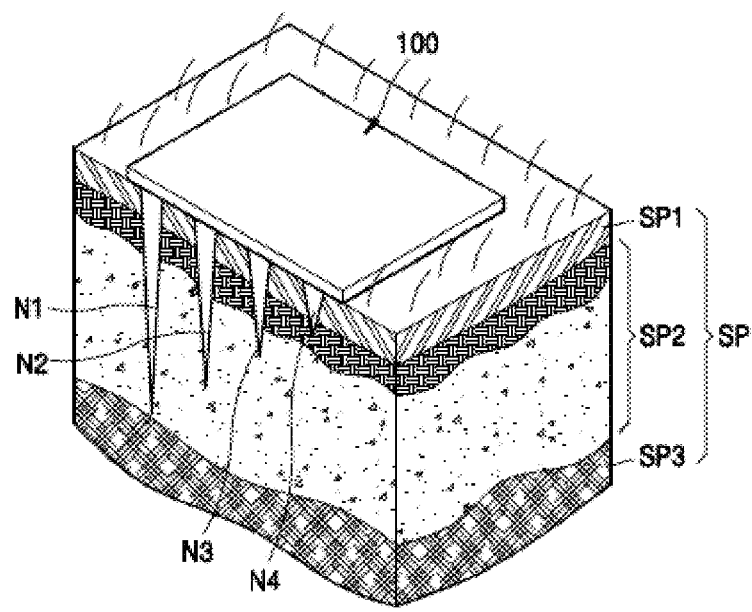
FIG. 2A is a diagram illustrating a biometric information measuring sensor attached to a specimen, according to an embodiment of the present disclosure.

FIG. 2A is a diagram illustrating a biometric information measuring sensor attached to a specimen, according to an embodiment of the present disclosure.

Referring to FIG. 1A and FIG. 2A, the needles N1, N2, N3, and N4 of the biometric information measuring sensor 100 penetrate or are inserted into and attached to the surface of a specimen SP. A depth of penetration or insertion into the specimen SP may differ depending on the lengths of the needles N1, N2, N3, and N4 of the biometric information measuring sensor 100. The specimen SP has an epidermis SP1, a dermis SP2, and a hypodermis SP3 below the surface thereof. A blood vessel may be located below the dermis SP2. The first needle N1, the longest of the needles N1, N2, N3, and N4 of the biometric information measuring sensor 100, penetrates or is inserted into a lower portion of the dermis SP2 or into the hypodermis SP3. When the biometric information measuring sensor 100 is attached to the specimen SP, the end-point of the first needle N1 may penetrate down to a location where a portion of capillaries may exist, but may not penetrate or be inserted into an area where general arteriola or venula may exist.

The specimen SP may be a human or an animal, or a portion of a human or an animal. Examples of various bio-markers existing in the blood vessel of the specimen SP include glucose, C-reactive protein (CRP), vitamin, aspartate aminotransferase (AST), alanine aminotransferase (ALT), glutaminate, uric acid, potassium, sodium, calcium, various female hormones, etc. Bio-markers existing in the blood vessel of the specimen SP may escape from the blood vessel due to diffusion, may exist in a body fluid such as, for example, intercellular fluid, sweat, saliva, etc., and may have a concentration that gradually decreases in accordance with a diffusion distance from the blood vessel. Thus, when one biometric information measuring sensor is divided into multiple of bio-marker measuring areas, and lengths of the needles N1, N2, N3, and N4 in respective measuring areas is diversified, various bio-markers may be simultaneously measured according to the concentration and lengths of the needles N1, N2, N3, and N4. Various bio-markers may be simultaneously measured in accordance with the location of the specimen SP by calculating appropriate lengths of the needles N1, N2, N3, and N4 for measured concentration values of each bio-marker, and by applying the result to the biometric information measuring sensor.

The bio-marker to be measured in FIG. 2A may be denoted as a target biomolecule. An enzyme capable of combining with a particular biomolecule may be coated to a surface of the first needle N1 arranged on the first working electrode 22 to detect a desired target biomolecule. This enzyme may be denoted as a probe biomolecule. The probe biomolecule may change an electric reaction corresponding to an electric stimulus inside the specimen SP. The probe biomolecule may be selected depending on the type of target biomolecule to be detected.

Different probe biomolecules may be coated on each of the needles N1, N2, N3, and N4. A first probe biomolecule may be coated to the surface of the first needle N1 of the first electrode 22, a second probe biomolecule may be coated to the surface of the second needle N2 of the second electrode 24, a third probe biomolecule may be coated to the surface of the third needle N3 of the third electrode 26, and a fourth probe biomolecule may be coated to the surface of the fourth needle N2 of the fourth electrode 28. The types of the first through fourth biomolecules are not limited.

The first through fourth biomolecules may be identical, and may be able to detect concentration differences of identical target biomolecules depending on the location on the specimen SP. In addition, the first through fourth biomolecules may include different types of probe biomolecules. Various bio-markers existing in the blood vessel of the specimen SP may have different concentrations. For example, glucose has a concentration of about 70 to about 120 mg/dL, CRP has a concentration of about 150 to about 500 ug/dL, and vitamin C has a concentration of about 0.4 to about 1.5 mg/dL. When a bio-marker having a relatively low concentration is to be measured, an inaccuracy of measurement due to diffusion of the bio-marker outside the blood vessel of the specimen SP may be prevented by applying a relatively long needle, inserting the needle near the blood vessel of the specimen SP and measuring the concentration. In addition, when a bio-marker having a relatively high concentration inside the blood vessel is to be measured, a measurement result with a relatively high accuracy may be obtained using relatively short needles.

Referring back to FIG. 2A the needles N1, N2, N3, and N4 have lengths such that the first needle N1 is inserted to a bottom portion of the dermis SP2, the second needle N2 is inserted to a middle portion of the dermis SP2, the third needle N3 is inserted to a top portion of the dermis SP2, and the fourth needle N4 is inserted to the uppermost portion of the dermis SP2. However, lengths of the needles N1, N2, N3, and N4 of the biometric information measuring sensor 100 are not limited thereto.

Figure 2B:
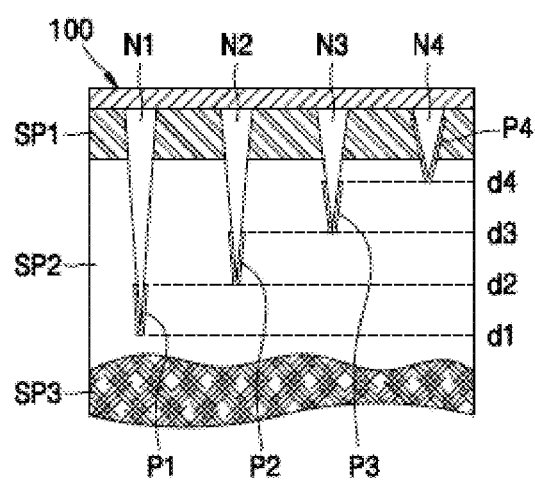
FIG. 2B is a diagram illustrating a structure of a needle with an attached enzyme, of the biometric information measuring sensor of FIG. 2A, according to an embodiment of the present disclosure.

FIG. 2B is a diagram illustrating a structure with an enzyme attached thereto, capable of combining with a particular biomolecule, such that the needle of the biometric information measuring sensor may detect a desired target biomolecule according to the embodiment illustrated in FIG. 2A.

Referring to FIG. 2A and FIG. 2B, an enzyme capable of combining with a particular biomolecule, that is, probe biomolecules P1, P2, P3, and P4, is coated on surfaces of needles N1, N2, N3, and N4 of the biometric information measuring sensor 100 to detect desired bio-markers, that is, target biomolecules. Probe biomolecules P1, P2, P3, and P4 may not need to be coated to the entire surfaces of needles N1, N2, N3, and N4. Probe biomolecules P1, P2, P3, and P4 may be coated to only end portions of needles N1, N2, N3, and N4.

For example, a first probe biomolecule P1 is coated only on the end portion of the first needle N1, and a second probe biomolecule P2 is coated only the end portion of the second needle N2. In addition, a third probe biomolecule P3 is coated only on the end portion of the third needle N3, and a fourth probe biomolecule P4 is coated only on the end portion of the fourth needle N4. The first needle N1, the second needle N2, the third needle N3, and the fourth needle N4 penetrate or are inserted into the specimen SP to respective depths d1, d2, d3, and d4 (d1>d2>d3>d4). The first probe molecule P1 is only coated on the first needle N1 in an area between the depth d1, which is the end portion of the first needle N1, and the depth d2, which is an end portion of the second needle N2. The second probe molecule P2 is only coated on the second needle N2 in an area between the depth d2 and the depth d3, which is the end portion of the third needle N3. The third probe molecule P3 is only coated on the third needle N3 in an area between the depth d3 and the depth d4, which is the end portion of the fourth needle N4. In addition, the fourth probe molecule P4 is only coated on the fourth needle N4 in an area between the surface of the specimen SP and the depth d4.

Areas of attachment, where the probe biomolecules P1, P2, P3, and P4 are respectively attached to the needles N1, N2, N3, and N4, may correspond to bio-marker measuring depths of the needles N1, N2, N3, and N4 of the biometric information measuring sensor 100, according to an embodiment of the present disclosure. Bio-marker measuring depths may be divided by differentiating the areas of attachment of the biomolecules P1, P2, P3, and P4 of the respective needles N1, N2, N3, and N4 of the biometric information measuring sensor 100 inside the specimen SP.

The bio-marker having escaped from the blood vessel at a low portion of the dermis SP2 of the specimen SP, and being diffused in a direction toward the surface of the specimen SP, is first sensed in an area (d1 to d2) where the first probe biomolecule P1 attached to the end portion of the first needle N1 is arranged. As the bio-marker approaches the skin surface of the specimen SP, the bio-marker may be sensed in an area (d2 to d3) where the second probe biomolecule P2 attached to the end portion of the second needle N2 is arranged, in an area (d3 to d4) where the third probe biomolecule P3 attached to the end portion of the third needle N3 is arranged, and in an area where the fourth probe biomolecule P4 attached to the end portion of the fourth needle N4 is arranged.

The probe biomolecules P1, P2, P3, and P4 may be the same kind or different kinds of enzymes. A diffusion speed and a concentration change of the bio-marker may be detected by measuring a time during which a particular bio-marker reaches the measuring depth of respective needles N1, N2, N3, and N4 after having escaped from the blood vessel of the specimen SP, and by measuring the concentration at the respectively measured time. The concentration may be measured in attachment areas of the biomolecules P1, P2, P3, and P4 on the respective needles N1, N2, N3, and N4, as the particular bio-marker escapes from the blood vessel of the specimen SP and diffuses in a direction toward the surface of the specimen SP. An actual concentration of the bio-marker inside the blood vessel may be detected either by using a time difference for the bio-marker to reach an identical concentration value at the respective needles N1, N2, N3, and N4, or by using the bio-marker measured at the identical time at the respective needles N1, N2, N3, and N4.

Figure 2C:
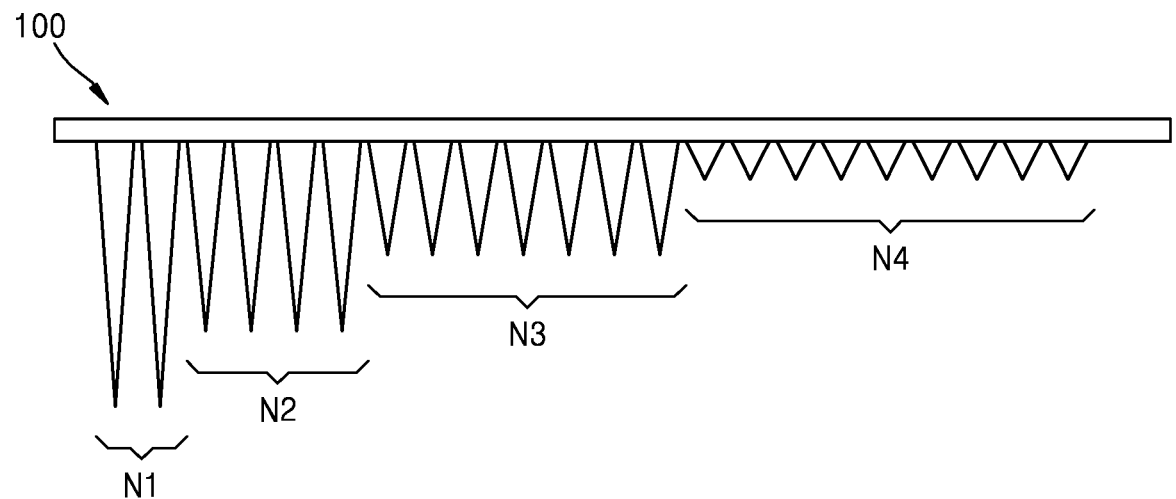
FIG. 2C is a diagram illustrating a needle of the biometric information measuring sensor, according to another embodiment of the present disclosure.

FIG. 2C is a diagram illustrating a needle of a biometric information measuring sensor, according to another embodiment of the present disclosure.

Referring to FIGS. 2B and 2C, the lengths of the respective needles N1, N2, N3, and N4 are different from each other, and the sizes of attachment areas for the probe biomolecules P1, P2, P3, and P4 may also be different from each other at the bio-marker measuring depth. Sizes of attachment areas of the probe biomolecules P1, P2, P3, and P4 on the needles N1, N2, N3, and N4 may be required to be the same, to compare values of bio-marker measurement results of the respective needles N1, N2, N3, and N4. A number of needles may be different for each of the needles N1, N2, N3, and N4 so that bio-marker measuring sizes of the respective needles N1, N2, N3, and N4 may be the same. In FIG. 2C, the first needle N1 has two needles, the second needle N2 has four needles, the third needle N3 has six needles, and the fourth needle N4 has nine needles, however, embodiments of the present disclosure are not limited thereto. For example, a number of needles of the second needle N2 may be greater than that of the first needle N1. Numbers of needles of the respective needles N1, N2, N3, and N4 may be arbitrarily changed so that attachment sizes of the probe biomolecules P1, P2, P3, and P4 on the needles N1, N2, N3, and N4 are the same.

Figure 3A:
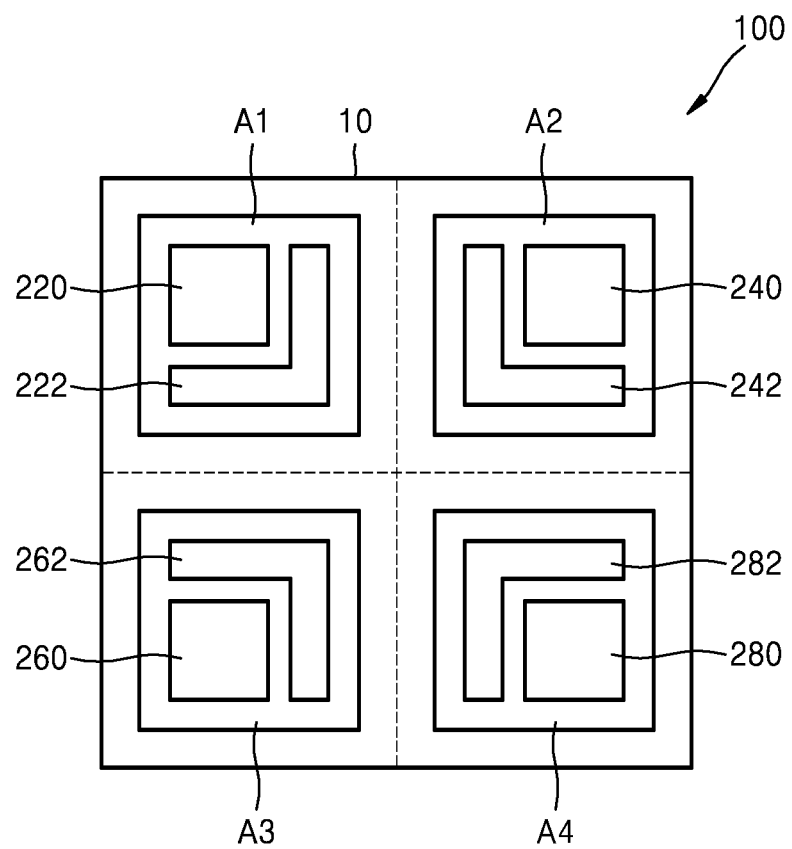
FIG. 3A and FIG. 3B are diagrams illustrating plan views of electrode structures of the biometric information measuring sensor, according to an embodiment of the present disclosure.
Figure 3B:
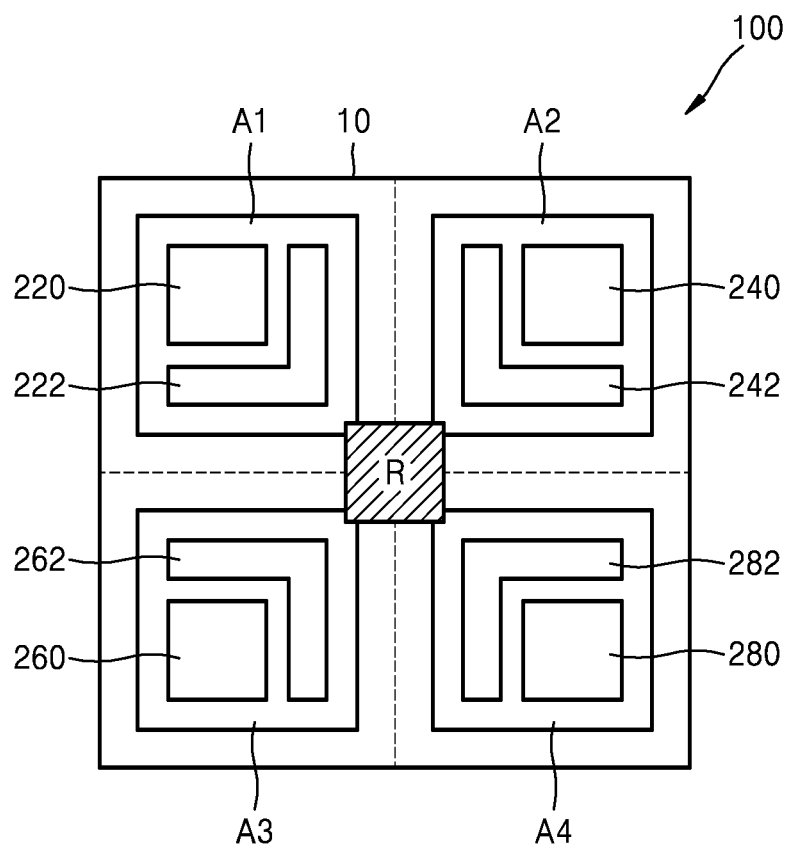

FIGS. 3A and 3B are diagrams illustrating plan views of electrode structures of a biometric information measuring sensor, according to an embodiment of the present disclosure.

Referring to FIG. 1A and FIG. 3A, the first electrode 22, the second electrode 24, the third electrode 26, and the fourth electrode 28 are respectively arranged on bio-marker measuring areas A1, A2, A3, and A4 in the base 10 of the biometric information measuring sensor 100. Respective electrodes include working electrodes 220, 240, 260, and 280 and counter electrodes 222, 242, 262, and 282, which are spaced apart from the working electrodes 220, 240, 260, and 280. For example, the first electrode 22 includes the first working electrode 220 and the first counter electrode 222, which is spaced apart from the first working electrode 220. The first needle N1 is arranged to have a protruded configuration in a form of a probe on the first working electrode 220 and the first counter electrode 222. The first counter electrode 222 has a relatively larger size than that of the first working electrode 220. This description may also be applied to, the second electrode 24, the third electrode 26, and the fourth electrode 28. Specifically, the counter electrodes 222, 242, 262, and 282 have larger surface sizes than those of the working electrodes 220, 240, 260, and 280 arranged on the electrodes 22, 24, 26, and 28. Also, the respective needles N1, N2, N3, and N4 are arranged on the working electrodes 220, 240, 260, and 280 and the counter electrodes 222, 242, 262, and 282.

The working electrodes 220, 240, 260, and 280, the counter electrodes 222, 242, 262, and 282, and the needles N1, N2, N3, and N4 may include conductive materials, such as, for example, metals, conductive metal oxides and conductive polymers. In detail, metals, such as Al, Cu, Au, Ag, Pt, Ti and Mo, or metal oxides, such as indium tin oxide (ITO), aluminum zinc oxide (AZO) and indium zinc oxide (IZO), may be included. The working electrodes 220, 240, 260, and 280 and the counter electrodes 222, 242, 262, and 282 may have flat surfaces that are in contact with and attached to the dermis SP1 of the specimen SP.

The needles N1, N2, N3, and N4 are arranged to protrude vertically upward from surfaces of the working electrodes 220, 240, 260, and 280 and the counter electrodes 222, 242, 262, and 282, have a width that gradually reduces toward an end portion, and have an end portion with a sharp shape. Lengths of the needles N1, N2, N3, and N4 protruding from surfaces of the working electrodes 220, 240, 260, and 280 and the counter electrodes 222, 242, 262, and 282 may be selected depending on thicknesses of the epidermis SP1, the dermis SP2, and the hypodermis SP3 of the specimen SP. Thicknesses of the epidermis SP1, the dermis SP2, and the hypodermis SP3 may vary depending on the area of the specimen SP, and the lengths of the needles N1, N2, N3, and N4 may be arbitrarily selected as being between several hundreds of microns and several thousands of microns, depending on the area of the specimen SP to be measured. In addition, widths of the needles N1, N2, N3, and N4 may be between several microns and several hundreds of microns. A cross-sectional shape of the needles N1, N2, N3, and N4 may be a circle, an ellipse, or a polygon, however, the shapes are not limited thereto. A portion of the cross-section shape of the needles N1, N2, N3, and N4 may have a round shape and another portion may have a polygon shape. The lengths of the needles N1, N2, N3, and N4 on the working electrodes 220, 240, 260, and 280 and the counter electrodes 222, 242, 262, and 282 may be the same in an identical bio-marker measurement area.

When the needles N1, N2, N3, and N4 are inserted into the specimen SP, bio-marker concentrations diffused from the blood vessel of the specimen SP may change in accordance with the epidermis SP1, the dermis SP2, and the hypodermis SP3 of the specimen SP. For example, when a glucose concentration is measured, the glucose concentration may gradually decrease depending on a distance from the blood vessel, and thus, glucose concentrations measured at respective needles N1, N2, N3, and N4 inserted into respectively different locations of the specimen SP may be different from each other. When an electric signal is applied to the working electrodes 220, 240, 260, and 280 and the counter electrodes 222, 242, 262, and 282, while probe biomolecules are attached to the needles N1, N2, N3, and N4, electric signals that different from each other may be output in accordance with the concentration of the target biomolecule combined with the probe biomolecule.

A principle of detecting the glucose from the bio-marker is described in greater detail below. Glucose oxidase or glucose dehydrogenase may be combined through coating the probe biomolecule on the needles N1, N2, N3, and N4 of the working electrodes 220, 240, 260, and 280. When the needles N1, N2, N3, and N4 are inserted into the specimen SP, the glucose that diffuses from the blood vessel of the specimen SP may be combined with the glucose oxidase on the needles N1, N2, N3, and N4. When an electric signal is applied to working electrodes 220, 240, 260, and 280, the glucose oxidase may be activated and the glucose may react with oxygen to produce gluconic acid and hydrogen peroxide ($H2O2$). In addition, an electron e may be produced as the hydrogen peroxide is decomposed. Due to the electron produced therein, a resistance value of the intercellular fluid inside the specimen SP may change and a measured electrical value may change. As a result, when the glucose is combined with the needles N1, N2, N3, and N4 of the working electrodes 220, 240, 260, and 280, a chemical reaction of glucose oxidation may occur, and electric signals, e.g., first through fourth electric signals, having magnitudes different from that of a reference electric signal may be detected depending on the glucose concentration.

In FIG. 3A, the counter electrodes 222, 242, 262, and 282 may function also as a reference electrode to act as a reference for voltages of the working electrodes 220, 240, 260, and 280. Alternatively, as illustrated in FIG. 3B, a reference electrode R at a ground state may be separately arranged from the counter electrodes 222, 242, 262, and 282.

Figure 4A:
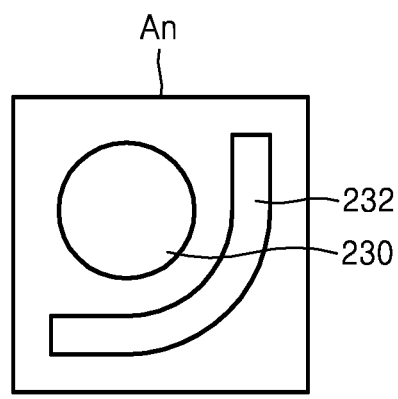
FIGS. 4A through 4C are diagrams illustrating electrode structures of the biometric information measuring sensor, according to an embodiment of the present disclosure.
Figure 4B:
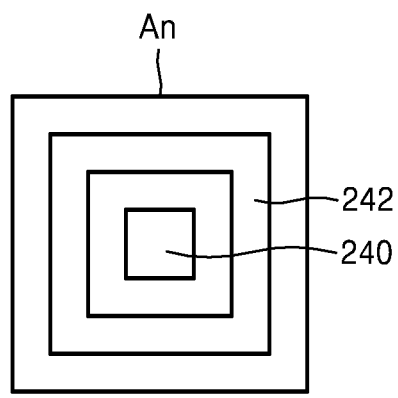
Figure 4C:
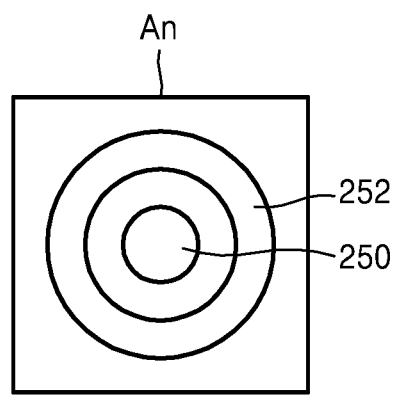

FIGS. 4A through 4C are diagrams illustrating electrode structures of a biometric information measuring sensor, according to an embodiment of the present disclosure.

As described in FIG. 1A, and FIGS. 3A and 3B, the bio-marker measuring areas A1, A2, A3, and A4 may be arranged to have different sizes and shapes. Additionally, shapes of the working electrodes 220, 240, 260, and 280, and the counter electrodes 222, 242, 262, and 282 may be arranged differently.

Referring to FIG. 4A, a working electrode 230 with a circular shape and a counter electrode 232 spaced apart from the working electrode 230 are arranged on a bio-marker measuring area An. The shape of the working electrode 230 may have a circular shape, a round shape, a polygon shape, etc. Referring to FIG. 4B, a counter electrode 242 is arranged to be spaced apart from and to surround a working electrode 240, which has a square shape. Referring to FIG. 4C, a counter electrode 252 is arranged to be spaced apart from and to surround a working electrode 250, which has a circular shape. The counter electrodes 232, 242, and 252 have larger sizes relative to those of the working electrodes 230, 240, and 250 in order to accommodate all signals generated in the working electrodes 230, 240, and 250. The needles illustrated in FIG. 1A, FIG. 3A, and FIG. 3B may be arranged on the working electrodes 230, 240, and 250 and the counter electrodes 232, 242, and 252. The working electrode 230 and the counter electrode 232 may have needles with identical lengths, but embodiments of the present disclosure are not limited thereto.

Figure 5:
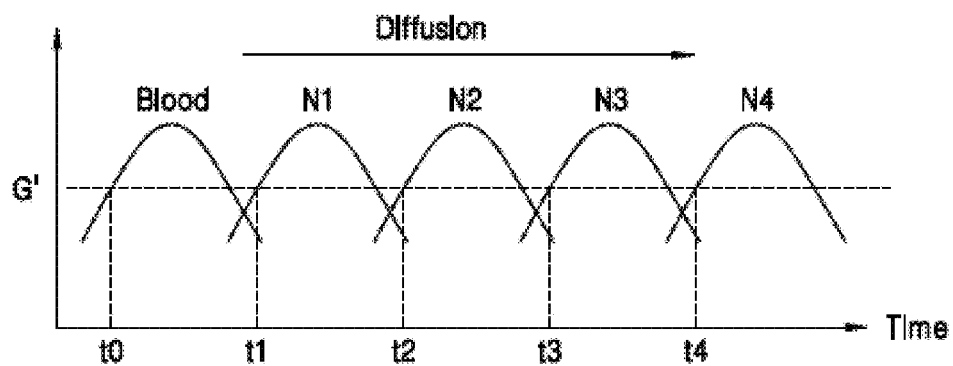
FIG. 5. is a graph showing a measurement of bio-markers diffused inside the specimen over time, using the biometric information measuring sensor, according to an embodiment of the present disclosure.

FIG. 5 is a graph showing a measurement of bio-markers diffused inside a specimen over time, by using a biometric information measuring sensor, according to an embodiment of the present disclosure. A horizontal axis of the graph denotes a time required for bio-markers discharged from the specimen SP of FIG. 2B, through diffusion, need to reach each of the needles N1, N2, N3, and N4 of the biometric information measuring sensor 100. A vertical axis denotes a bio-marker concentration discharged from the blood vessel of the specimen SP.

Referring to FIG. 2B and FIG. 5, the bio-marker produced from the blood of the specimen SP, for example, the glucose, may be included in the body fluid and diffused to the hypodermis SP3 and the dermis SP2 of the specimen SP.

At the initial stage of diffusion, the glucose concentration measured at the first needle N1 may be higher than that at the second needle N2, which is higher than that at the third needle N3, and which is higher than that at the fourth needle N4. In order for the glucose concentration at each of the needles N1, N2, N3, and N4 to reach an identical value G', the first needle N1 requires a time t1, the second needle N2 requires a time t2, the third needle N3 requires a time t3, and the fourth needle N4 requires a time t4. The time for bio-markers diffused from the blood to reach the respective needles N1, N2, N3, and N4 may vary depending on the specimen SP to be measured. The time may also vary depending on a condition or a length of time of the specimen.

The biometric information measuring sensor, according to an embodiment of the present disclosure, may include the needles N1, N2, N3, and N4 with various lengths, and may use a time t difference t2−t1, t3−t2, t4−t3 . . . , for the bio-marker to reach a certain concentration value G' at each of the needles N1, N2, N3, and N4. The biometric information measuring sensor may tabulate each of weights, and apply the result to a bio-marker concentration formula in the blood, as shown in Equation (1) below:

$$Cb1 = v1*C1 + v2*C2 + \ldots + vn*Cn \quad (1)$$

where Cb1 is a bio-marker inside the blood, v1, v2, . . . , vn are weights at each of the needles N1, N2, N3, and N4, and C1, C2, . . . , Cn are values of bio-marker concentrations measured at each of the needles N1, N2, N3, and N4. Bio-markers discharged and diffused from the blood of the specimen may experience a time lag due to a diffusion time through the body fluid or the interstitial fluid (ISF), and accordingly, a measurement error of bio-markers may exist. As described above, the biometric information measuring sensor 100, according to an embodiment of the present disclosure, may include the needles N1, N2, N3, and N4 with various lengths, may use weights v1, v2, . . . , vn applied in accordance with the time difference in reaching a certain value of bio-marker concentration at each of the needles N1, N2, N3, and N4, and may compensate for the measurement error.

Figure 6:
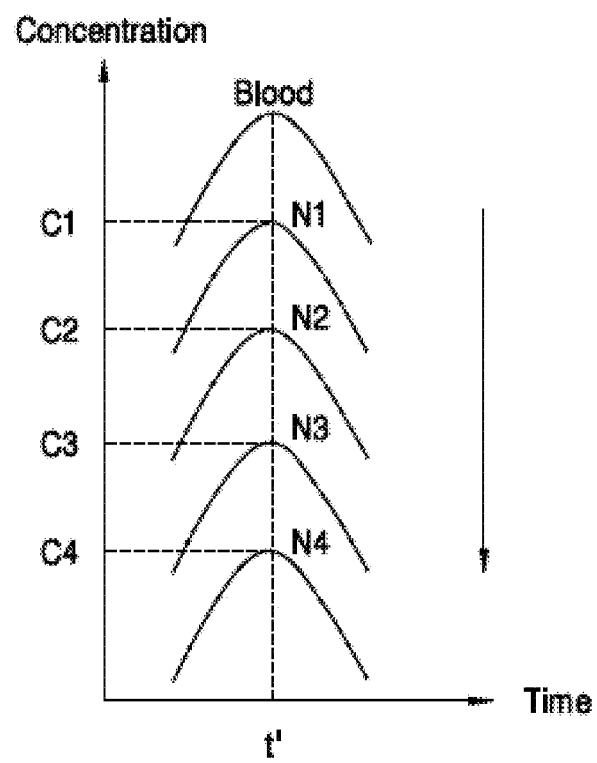
FIG. 6 is a graph showing measurement results of bio-markers diffused inside the specimen, obtained using the biometric information measuring sensor, being represented as concentration values for each measuring location, according to an embodiment of the present disclosure.

FIG. 6 is a graph showing measured results of bio-markers diffused inside the specimen, obtained by using the biometric information measuring sensor, being represented as concentration values for each measuring location, according to an embodiment of the present disclosure. A horizontal axis denotes a time during which a bio-marker discharged and diffused from the specimen SP in FIG. 2B may need to reach each of the needles N1, N2, N3, and N4 of the biometric information measuring sensor 100. A vertical axis denotes the bio-maker concentration discharged from the blood of the specimen SP.

Referring to FIG. 2B and FIG. 6, a bio-marker discharged from the blood of the specimen SP, for example, the glucose, may be included in the body fluid and diffused to the hypodermis SP3 and the dermis SP2 of the specimen SP. After an identical time has passed, the glucose concentration measured at the first needle N1 is higher than that at the second needle N2, which is higher than that at the third needle N3, and which is higher than that at the fourth needle N4. The biometric information measuring sensor, according to an embodiment of the present disclosure, may include the needles 1\11, N2, N3, and N4 with various lengths, may apply respective weights to values of bio-marker concentration at each of the needles N1, N2, N3, and N4 at a certain time t', and may apply the result to a bio-marker concentration formula in the blood, as shown in Equation (2) below:

$$Cb2=w1*C1+w2*C2+ \ldots +wn*Cn \quad (2)$$

where Cb1 is a bio-marker inside the blood vessel, w1, w2, ..., wn are concentration weights at each of the needles N1, N2, N3, and N4, and C1, C2, ..., Cn are values of bio-marker concentration measured at each of the needles N1, N2, N3, and N4.

Figure 7:
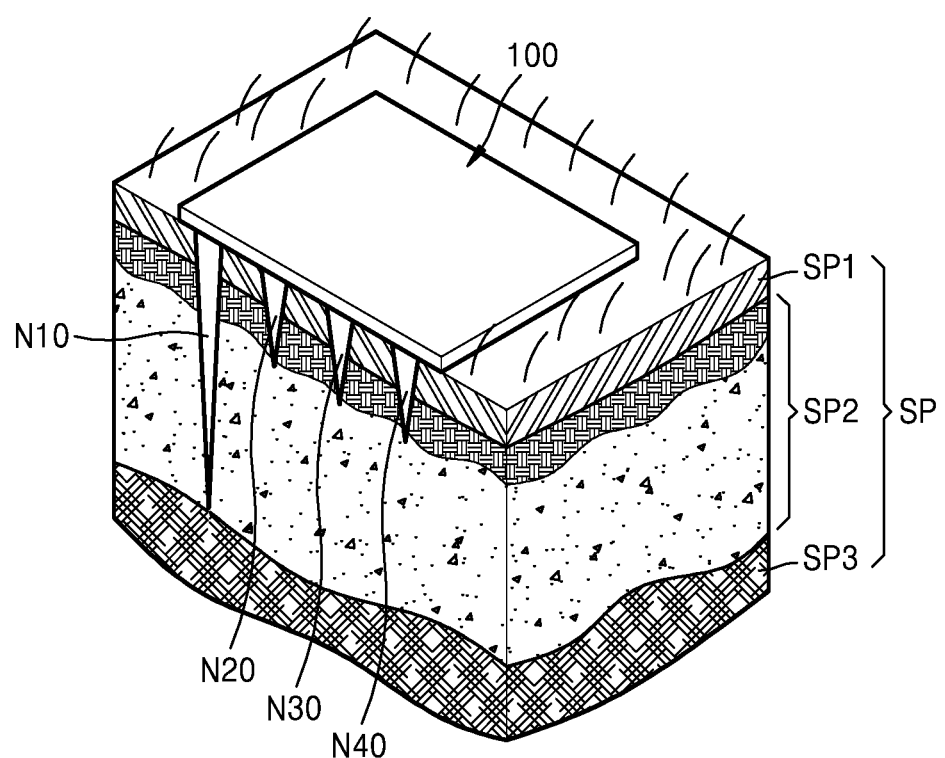
FIG. 7 is a diagram illustrating a biometric information measuring sensor, according to another embodiment of the present disclosure.

FIG. 7 is a diagram illustrating a biometric information measuring sensor, according to another embodiment of the present disclosure.

Referring to FIG. 7, and FIGS. 1 and 2, the biometric information measuring sensor 100 includes a plurality of needles N10, N20, N30, and N40, each having lengths that are different from each other. The first needle N10 has a relatively longer length than those of the second, third, and fourth needles N20, N30, and N40. The second needle N20, the third needle N30, and the fourth needle N40 have identical or substantially identical lengths.

When biometric information of the specimen SP is to be measured by using the biometric information measuring sensor 100 of FIG. 7, the first needle N10 through the fourth needle N40 penetrate or are inserted into the epidermis SP1, the dermis SP2 and the hypodermis SP3 of the specimen SP through the surface of the specimen SP. When an identical enzyme, that is, the probe biomolecule, is coated to the first needle N10 through the fourth needle N40 for measuring the same bio-marker, the bio-marker concentration is measured in accordance with the location of the specimen SP and the depth from the surface of the specimen SP. As illustrated in FIG. 5, the bio-marker concentration in the blood vessel of the specimen SP may be calculated by considering the time difference with respect to measurement results of the first needle N10 and other needles N20, N30, and N40. Also, as illustrated in FIG. 6, the bio-marker concentration in the blood vessel of the specimen SP may be calculated by considering the measurement depth. In addition, the bio-marker concentration at the same or similar depth from the surface of the specimen SP and at locations different from each other may be measured by using the second needle N20 through the fourth needle N40. In this case, the bio-marker concentration diffused from the blood vessel of the specimen SP before reaching the second needle N20 through the fourth needle N40 may be estimated by using the value of the bio-marker concentration measured at the first needle N10 and the time difference.

Figure 8:
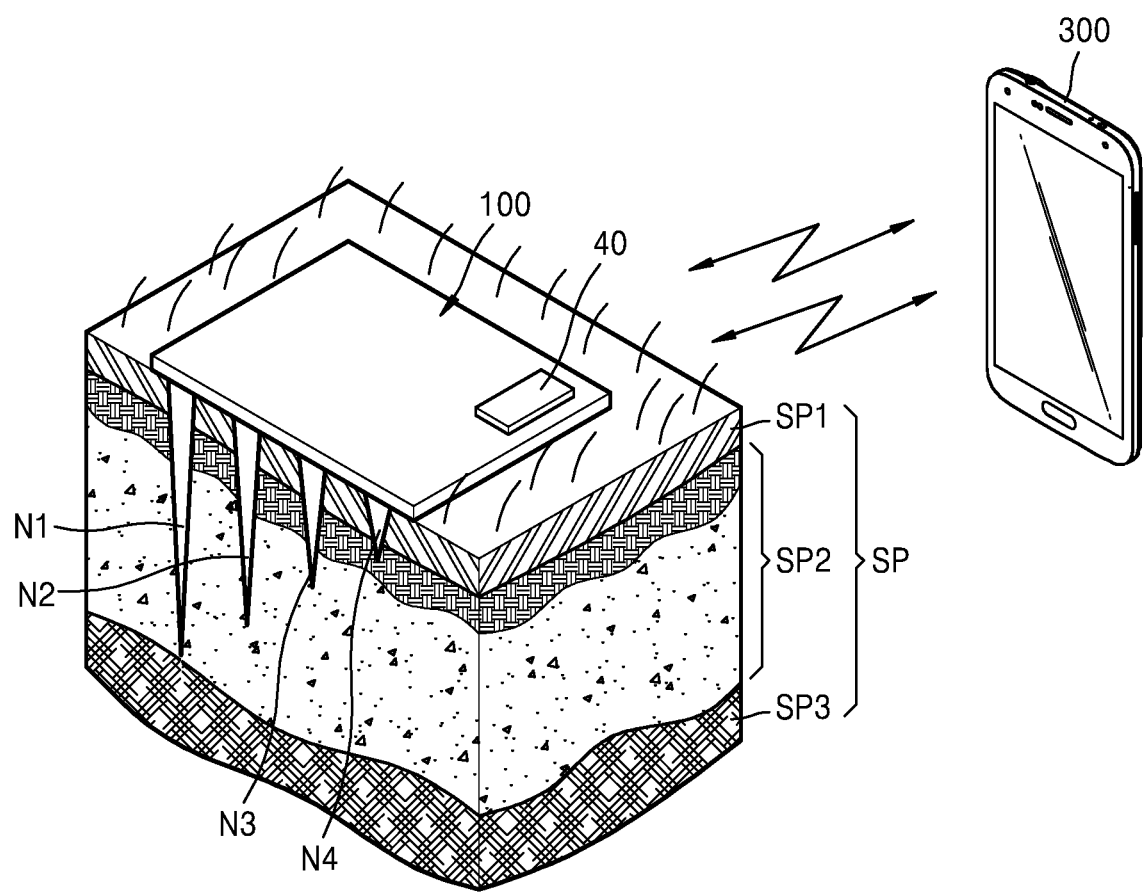
FIG. 8 is a diagram illustrating transmission of biometric information measured from the specimen, using the biometric information measuring sensor, to a terminal unit, according to an embodiment of the present disclosure.

FIG. 8 is a diagram illustrating transmission of biometric information measured from the specimen, by using the biometric information measuring sensor, to a terminal unit, according to an embodiment of the present disclosure.

Referring to FIG. 8, an electric signal that is measured at the needles N1, N2, N3, and N4 by attaching the biometric information measuring sensor 100 to the specimen SP is transmitted to a terminal unit 300 outside the biometric information measuring sensor 100 via a transmitter 40 arranged on a portion of the biometric information measuring sensor 100. In FIG. 8, the electric signal measured in the biometric information measuring sensor 100 is wirelessly transmitted to the terminal unit 300 via the transmitter 40; however, the electric signal may be directly transmitted by connecting the biometric information measuring sensor 100 and the terminal unit 300 by wire. The terminal unit 300 may be embodied as a device that includes an information processing unit, such as, for example, a mobile device (e.g., a smart phone or tablet), a personal computer (PC), a storage unit, or a display. The terminal unit 300 may also be embodied as a wearable device or other electronic device used for healthcare.

Figure 9:
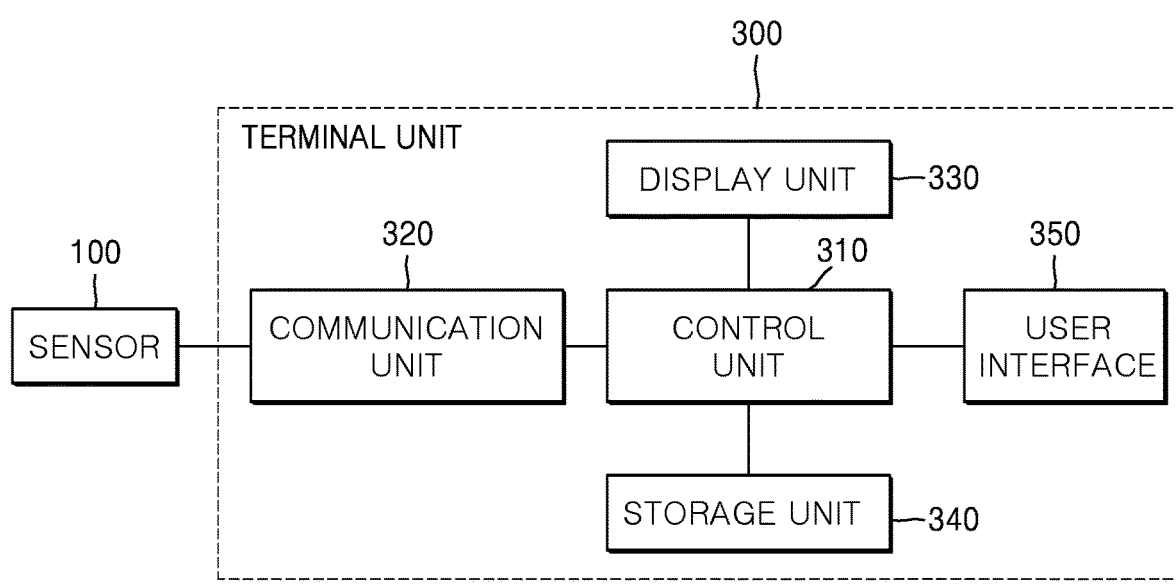
FIG. 9 is a block diagram illustrating a biometric information analysis system including a biometric information measuring sensor, according to an embodiment of the present disclosure.

FIG. 9 is a block diagram illustrating a biometric information analysis system including a biometric information measuring sensor, according to an embodiment of the present disclosure.

Referring to FIG. 9, the electric signal measured from the biometric information measuring sensor 100 may be transmitted to a communication unit 320 of the terminal unit 300. The transmitted electric signal may be used in a certain algorithm in a control unit 310 of the terminal unit 300 to produce resulting values relating to the biometric information of the specimen SP. The biometric information measured by the biometric information measuring sensor 100 may be stored in the storage unit 340, and a change value may be calculated by comparing the measured biometric information with biometric information of the specimen SP that was previously stored in the storage unit 340. A biometric information measurement result of the specimen SP or a comparison result may be output through the display unit 330 of the terminal unit 300. The biometric information of the specimen SP that is measured by the biometric information measuring sensor 100 may be set up based on user interaction via a user interface 350.

Figure 10:
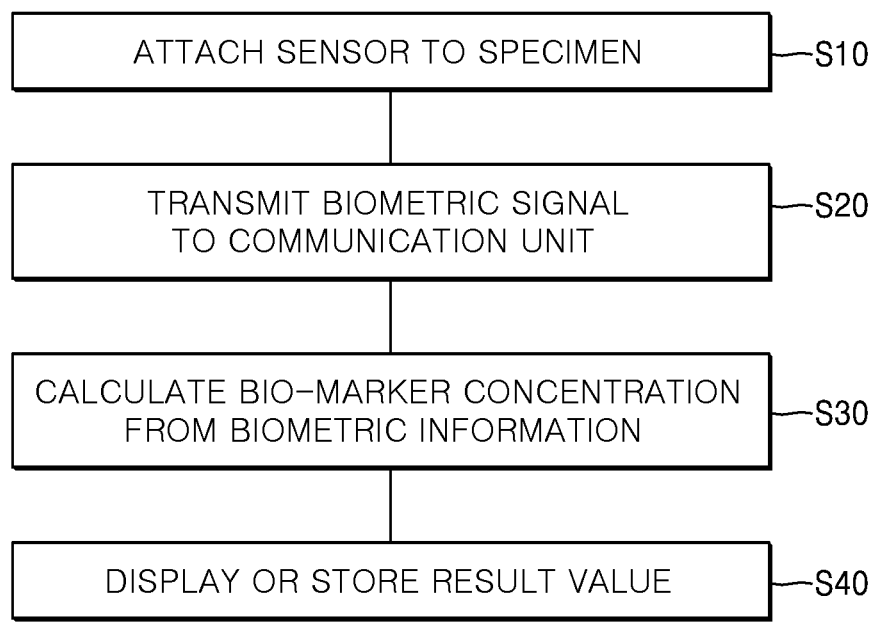
FIG. 10 is a flowchart illustrating a method of measuring biometric information using a biometric information measuring sensor, according to an embodiment of the present disclosure.

FIG. 10 is a flowchart illustrating a method of measuring biometric information by using a biometric information measuring sensor, according to an embodiment of the present disclosure.

Referring to FIG. 9 and FIG. 10, the biometric information measuring sensor 100 is attached to the specimen SP, in step S10. The biometric information measuring sensor may include the needles N1, N2, N3, and N4 with properly adjusted lengths depending on the bio-marker used to measure biometric information and a body part of the specimen SP. The electric signal measured by the biometric information measuring sensor 100 is transmitted to the communication unit of the external terminal unit 300, in step S20. In the terminal unit 300, a corresponding bio-marker concentration is calculated using the biometric electric signal transmitted from the biometric information measuring sensor 100, in step S30. Also, a calculated result value is displayed at the display unit 330 or is stored in the storage unit 340, in step S40.

While the disclosure has been shown and described with reference to certain embodiments thereof, it will be understood by those of ordinary skill in the art that various changes in form and detail may be made therein without departing from the spirit and scope of the disclosure as defined by the appended claims and their equivalents.

What is claimed is:

1. A biometric information measuring sensor comprising:
a base comprising a plurality of bio-marker measuring areas;
a plurality of electrodes, each of the plurality of electrodes being disposed on a respective one of the plurality of bio-marker measuring areas, and each of the plurality of electrodes comprising a working electrode and a counter electrode spaced apart from the working electrode; and a plurality of needles, each of the plurality of needles being disposed on a respective one of the plurality of electrodes, wherein the plurality of needles includes at least a first needle set including a same first length of needles, coated with a first probe biomolecule positioned at a first depth and a second needle set including a same second length of needles, coated with a second probe biomolecule positioned at a second depth, wherein the first depth is different from the second depth, wherein each of the first probe biomolecule and the second probe biomolecule is coated on only end portions of the needles included in the first needle set and the needles included in the second needle set, respectively, and wherein the first length of needles and second length of needles are different.

2. The biometric information measuring sensor of claim 1, wherein at least one of the plurality of electrodes further comprises a reference electrode spaced apart from the counter electrode.

3. The biometric information measuring sensor of claim 1, wherein the counter electrode has a larger surface area than that of the working electrode.

4. The biometric information measuring sensor of claim 3, wherein each of the plurality of needles is disposed on the working electrode and the counter electrode of each of the plurality of electrodes.

5. The biometric information measuring sensor of claim 1, wherein the first probe biomolecule and the second probe biomolecule are an enzyme.

6. The biometric information measuring sensor of claim 1, wherein the plurality of bio-marker measuring areas comprises a first bio-marker measuring area having the first needle set with the first length that is longer than those of remaining needle sets in remaining bio-marker measuring areas of the plurality of bio-marker measuring areas.

7. The biometric information measuring sensor of claim 1, wherein the first probe biomolecule and the second probe biomolecule are attached at different distances from the base.

8. The biometric information measuring sensor of claim 1, wherein sizes of areas where the first probe biomolecule is attached to the first needle set and the second probe biomolecule is attached to the second needle set are substantially identical.

9. The biometric information measuring sensor of claim 8, wherein the first needle set, and the second needle set of the plurality of needles have a different number of needles.

10. A biometric information measuring system, the system comprising:

a biometric information measuring sensor comprising a base with a plurality of bio-marker measuring areas, a plurality of electrodes, and a plurality of needles, each of the plurality of electrodes being disposed on a respective one of the plurality of bio-marker measuring areas, each of the plurality of electrodes comprising a working electrode and a counter electrode spaced apart from the working electrode, and each of the plurality of needles being disposed on a respective one of the plurality of electrodes, wherein the plurality of needles includes a first needle set including a same first length of needles coated with a first probe biomolecule positioned at a first depth and a second needle set including a same second length of needles coated with a second probe biomolecule positioned at a second depth, wherein the first depth is different from the second depth; and a terminal unit configured to calculate biometric information of a specimen from an electric signal transmitted from the biometric information measuring sensor, wherein each of the first probe biomolecule and the second probe biomolecule is coated on only end portions of the needles included in the first needle set and the needles included in the second needle set, respectively, and wherein the first length of needles and second length of needles are different.

11. The biometric information measuring system of claim 10, wherein at least one of the plurality of electrodes comprises a reference electrode spaced apart from the counter electrode.

12. The biometric information measuring system of claim 10, wherein each of the plurality of needles is disposed on the working electrode and the counter electrode of each of the plurality electrodes, and comprises an enzyme.

13. The biometric information measuring system of claim 12, wherein the first needle set and the second needle set have the enzyme attached at different distances from the base.

14. The biometric information measuring system of claim 12, wherein sizes of areas where the enzyme is attached to the two or more needles are substantially identical.

* * * * *